(12) United States Patent
Bertoletti

(10) Patent No.: US 6,336,810 B1
(45) Date of Patent: Jan. 8, 2002

(54) RING FOR USE IN PREPARING TEETH FOR RESTORATION

(75) Inventor: Raymond L. Bertoletti, Oakland, CA (US)

(73) Assignee: Danville Materials, San Ramon, CA (US)

(*) Notice: Subject to any disclaimer, the term of this patent is extended or adjusted under 35 U.S.C. 154(b) by 0 days.

(21) Appl. No.: 09/406,361

(22) Filed: Sep. 28, 1999

Related U.S. Application Data

(60) Provisional application No. 60/127,488, filed on Apr. 2, 1999.

(51) Int. Cl.$^7$ .............................. A61C 5/04; A61C 3/00
(52) U.S. Cl. .......................... 433/39; 433/148; 433/155
(58) Field of Search ........................... 433/148, 39, 40, 433/155, 138, 139

(56) References Cited

U.S. PATENT DOCUMENTS

| | | | |
|---|---|---|---|
| 164,870 A | * | 6/1875 | Palmer ..................... 433/139 |
| 348,628 A | * | 9/1886 | Hewett ...................... 433/39 |
| 388,619 A | * | 8/1888 | Booth ....................... 433/29 |
| 532,723 A | | 1/1895 | Dennis |
| 644,705 A | | 3/1900 | Evans |
| 677,268 A | | 6/1901 | Power |
| 692,274 A | | 2/1902 | Gumaer |
| 796,120 A | * | 8/1905 | Green ....................... 433/39 |
| 867,379 A | | 10/1907 | Kaufman |
| 1,378,748 A | * | 5/1921 | Wiggins .................... 433/39 |
| 2,083,077 A | | 6/1937 | Mayer |
| 2,088,208 A | | 7/1937 | Kassap |
| 2,567,101 A | | 9/1951 | Carpenter |
| 2,646,622 A | | 7/1953 | Christie et al. |
| 2,651,841 A | | 9/1953 | Peterson |
| 2,790,238 A | | 4/1957 | Trangmar |
| 3,074,169 A | | 1/1963 | Freeman |
| 3,463,157 A | | 8/1969 | Hunt |
| 3,548,500 A | | 12/1970 | Cohen |
| 4,269,190 A | | 5/1981 | Behney |
| 4,303,389 A | | 12/1981 | Salsarulo |
| 4,718,852 A | * | 1/1988 | Galler ....................... 433/148 |
| 4,824,365 A | | 4/1989 | Von Weissenfluh |
| 4,986,752 A | | 1/1991 | Graves |
| 5,607,302 A | | 3/1997 | Garrison et al. |

OTHER PUBLICATIONS

Danville Materials, Product Update: "Danville, Once Again Driving the Competition Crazy," 1998.

Danville Engineering, Price List: "Innovative Dental Products," pp. 1–4, 1997.

Darway, "Restorative Technique: Delivering Excellent Contacts and Proximal Contours with the Palodent Contoured Sectional Matrix System," Dental Products Report Europe, 1999 Technique & Product Review, pp. 24–25.

Darway, "Metal," Reality, vol. 11, Sec. 1 & 2, pp. 428–432, 1997.

Garrison, "Restorative Technique: direct restorations with the Composi–Tight Sectional Matrix System from Garrison Dental Solutions," Dental Products Report Europe, 1999 Technique & Product Review, pp. 10.

Garrison, Product Brochure: "Composi–Tight: Sectional Matrix Retainer System. For Tight, Anatomical Contacts on Every Posterior Composite Restoration".

* cited by examiner

Primary Examiner—Todd E. Manahan
(74) Attorney, Agent, or Firm—Cooley Godward LLP

(57) ABSTRACT

The invention is an open-ended ring used in the preparation of a tooth for a restorative procedure. The ring is used in conjunction with a shield to secure the shield between a tooth to be restored and an adjacent tooth. The result is a close contact being formed between the two teeth after restoration.

23 Claims, 4 Drawing Sheets

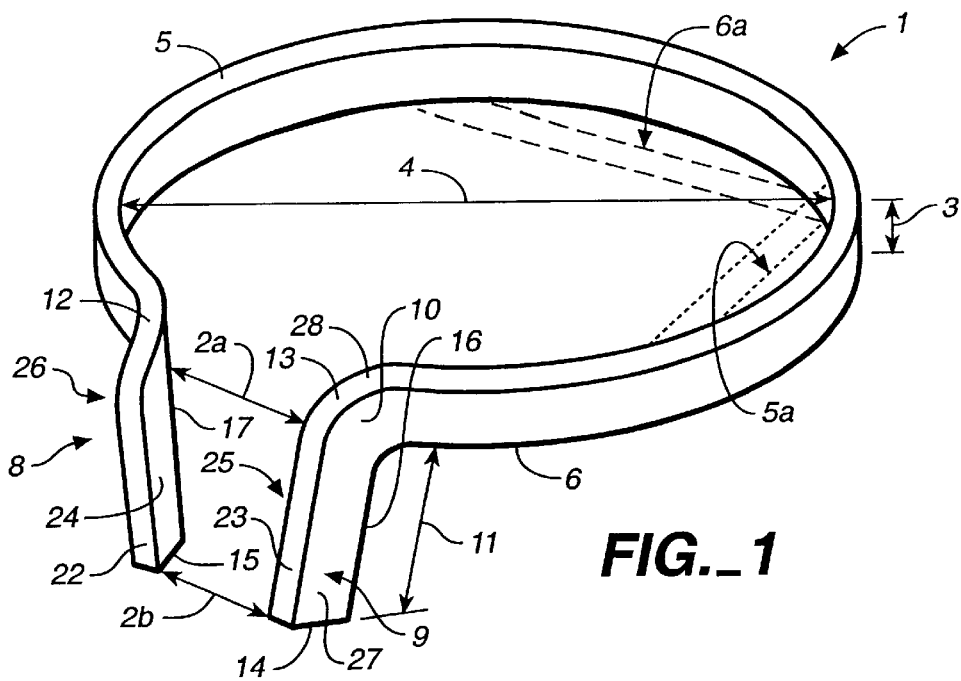
FIG._1
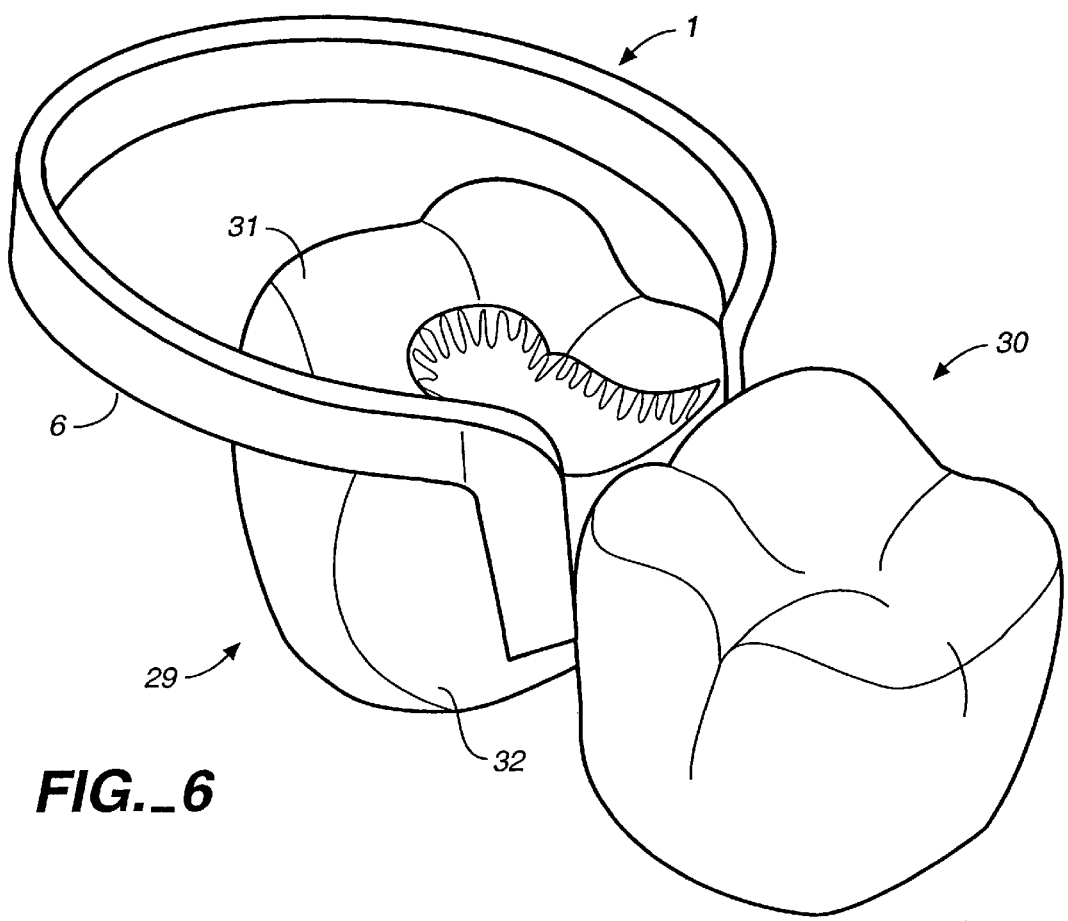
FIG._6

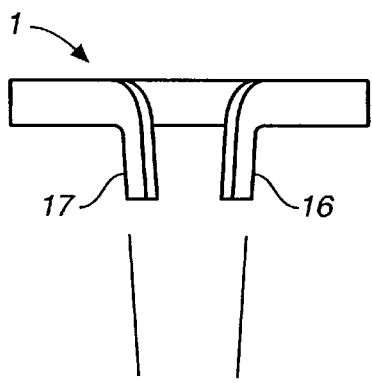
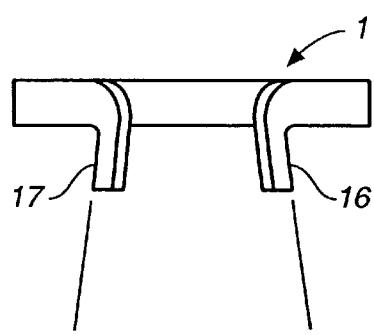
FIG._2    FIG._3
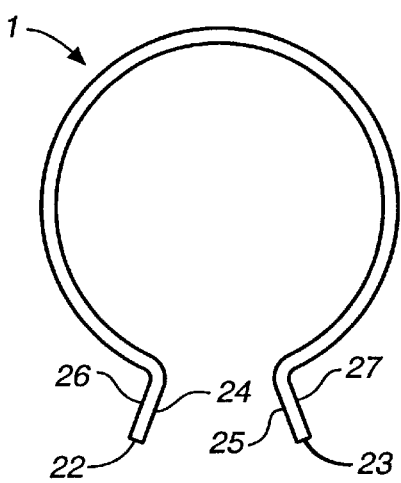
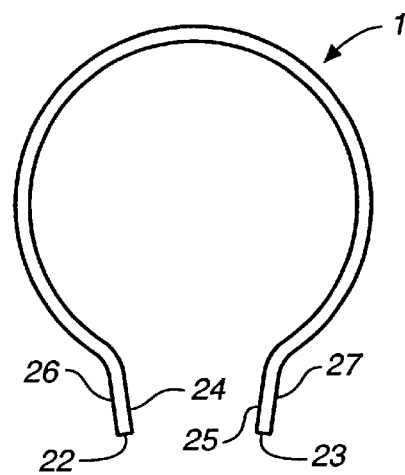
FIG._4    FIG._5
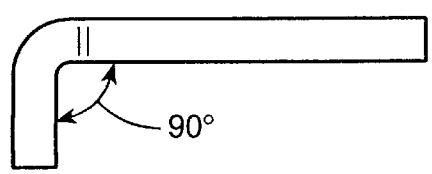
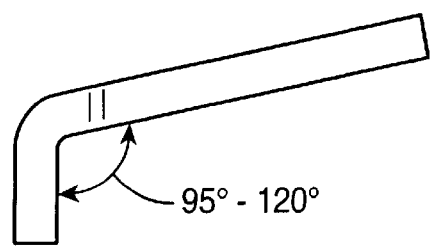
FIG._9A
*(PRIOR ART)*
FIG._9B

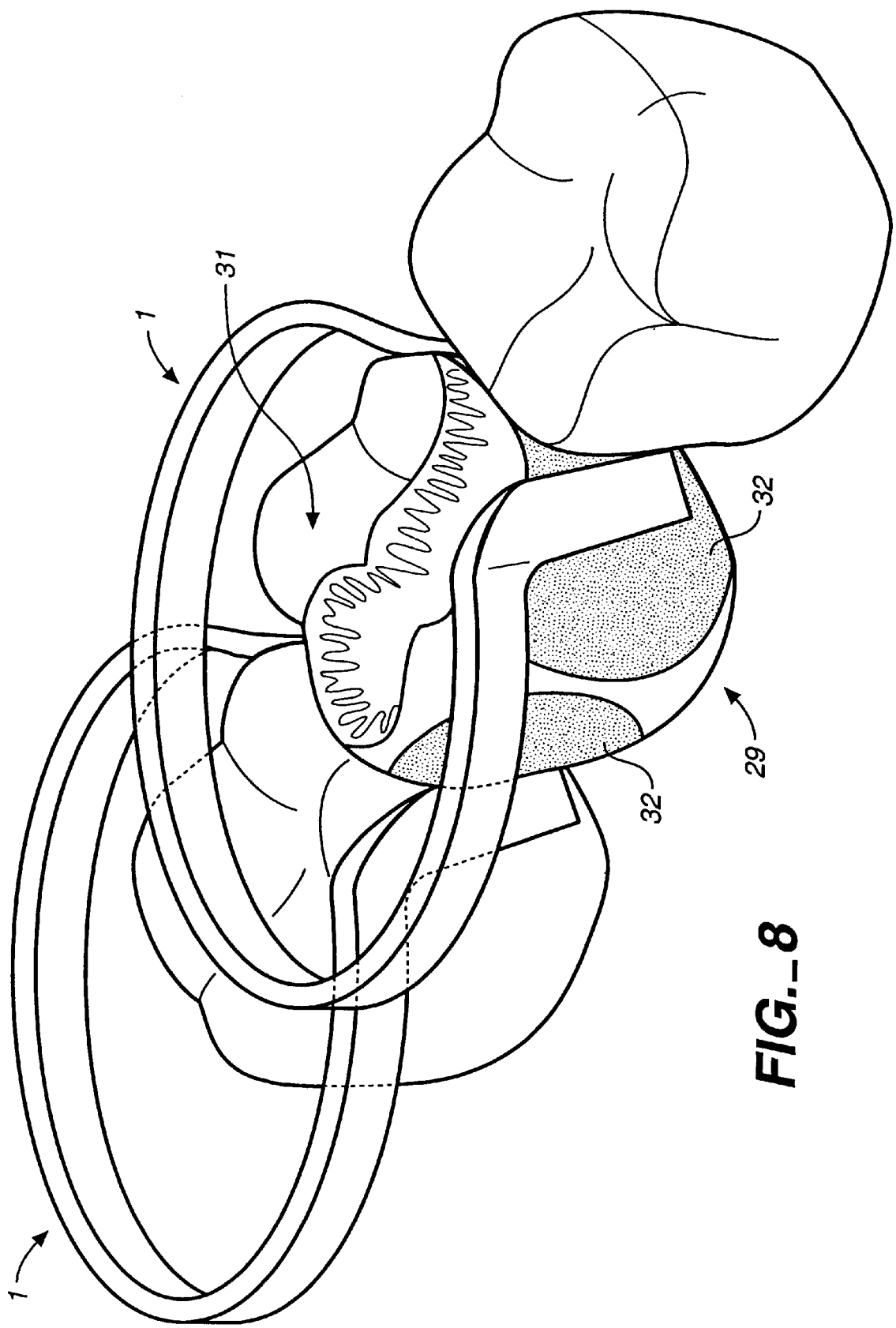
FIG._8

RING FOR USE IN PREPARING TEETH FOR RESTORATION

CONTINUING DATA

This application is a continuation-in-part of U.S. Application Serial No. 60/127,488, filed Apr. 2, 1999, which is incorporated herein by reference in its entirety.

TECHNICAL FIELD

This invention relates to an apparatus and method for preparing one or more teeth for restoration. The invention is useful for dental applications.

BACKGROUND

Today, increasing numbers of patients are requesting posterior composites for aesthetic and health concerns. However, many dentists are reluctant to use them because there has been no reliable and convenient way to obtain a tight contact between teeth. A tight contact between teeth is desirable to avoid grinding and further damage to the teeth and drifting of teeth. Customarily, the means for preparing a tooth for restoration with a restorative material has been the following; a contact shield and a ring are placed between two teeth, one of which is a select tooth for restoration. The tines of the ring press the select tooth away from its adjacent tooth and press the shield against the select tooth. The select tooth is then ready for a number of restorative processes. Several different types of rings exist in the art, though these rings have several common problems. First, the rings are not very retentive when placed between two teeth. Second, they are not able to be stacked upon one another, allowing for more than one tooth to be restored concurrently or allowing for a tighter grip on one select tooth. The apparatus of the invention provides a more retentive ring, with better separating force, that can be used in a normal or inverted orientation, used in normal or wide preps, as well as being able to be stacked upon one another.

SUMMARY OF THE INVENTION

One aspect of this invention is a flexible, open-ended ring, with top and bottom surfaces, each forming a plane, the ring having two downward extending tines, permanently incorporated into the open ends of the ring, each tine at an obtuse angle from the bottom plane surface of the ring. Each tine has a top edge, a bottom edge, an outward edge, an inward edge, an inner face, and an outer face. The bottom edge of each tine converges towards the other.

Another aspect of this invention is a method of preparing a tooth for restoration. The method comprises (a) placing a shield between two or more teeth, one tooth being a select tooth for restoration and having an upper flat table; (b) inserting between the select tooth and a tooth adjacent to the select tooth, a flexible, open-ended ring, with top and bottom surfaces, each forming a plane, the ring having two downward extending tines, permanently mounted to the open ends of the ring, each tine at an obtuse angle from the bottom plane surface of the ring, wherein each tine has a top edge, a bottom edge, an outward edge, an inward edge, an inner face, and an outer face, the bottom edge of each tine converging towards the other; and (c) causing the tines of the ring to gently press the select tooth away from the adjacent tooth, and to secure the shield against the select tooth. This method reduces toggling of the select tooth. By having the tines extending at an obtuse angle relative to the ring's bottom surface plane, the ring holds the shield more securely in place than a standard ring known in the art that has the tines extending at a right angle to the ring's bottom surface.

Another aspect of the invention is a kit for preparing teeth for restoration. The kit comprises (a) one or more flexible, open-ended rings as herein described; and (b) one or more shields suitable for use with the rings in accordance with the method described.

Other aspects of the invention will be apparent to one of skill in the art upon reading the following specification and claims.

BRIEF DESCRIPTION OF THE DRAWINGS

FIG. 1 is a perspective view of an open-ended ring with two downwardly extending tines.

FIG. 2 is a front view of a ring with first tine inward edge converging towards second tine inward edge.

FIG. 3 is a front view of a ring with first tine inward edge diverging away from second tine inward edge.

FIG. 4 is a top view of the ring of FIG. 3.

FIG. 5 is a top view of the ring of FIG. 2.

FIG. 6 is a perspective view of a shield and a ring positioned between two teeth.

FIG. 8 is a perspective view of two shields and two rings being used concurrently.

FIG. 9A is a side view of a prior art ring.

FIG. 9B is a side view of the ring of FIG. 1.

DETAILED DESCRIPTION AND PRESENTLY PREFERRED EMBODIMENTS

Definitions

Figure 7:
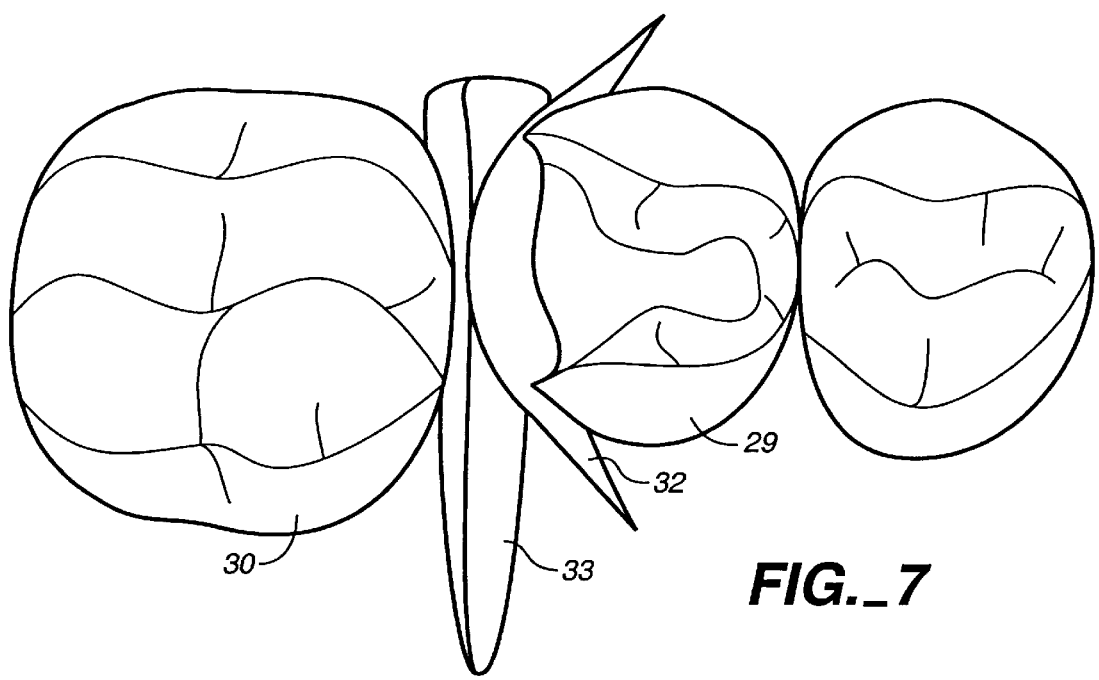
FIG. 7 is a top view of a shield and a wedge positioned between two teeth.

Restoration of a tooth is a method for returning it to its normal morphology or close to its normal morphology and anatomy through the use of restorative materials.

The types of restorative processes performed with the disclosed device are known in dentistry as class II type restorations. Class II restorations of the type where the disclosed device is particularly useful involve the occlusal tooth surface and either the mesial or distal interproximal region of the tooth. The area where two adjacent teeth touch is referred to as the interproximal region. When the mesial or distal interproximal section of a tooth needs to be removed due to a carious lesion, the disclosed device and method allows the tooth anatomy to be restored in an optimal way replacing in an acceptable manner the original interproximal tooth contact.

Restorative materials are those materials commonly used by one skilled in the art of dentistry to restore a damaged tooth and include, but are not limited to, composites, silver, gold, porcelain, almagams, alloys, wax, temporaries, and other known restorative materials.

The plane of the ring is defined as the flat or level surface formed by the top or bottom surfaces of the ring.

An acute angle is an angle less than 90 degrees.

An obtuse angle is an angle between 90 and 180 degrees.

A shield is a protective device or structure that can be placed between two teeth.

A tooth can belong to a human or non-human animal, and can be contained within the animal or outside of the animal. A tooth can be a cast or replica of a tooth obtained from or similar to a human or non-human animal. A tooth can be an incomplete or a complete tooth.

Occlusal Offset refers to the angulation of the plane of the ring relative to the occlusal plane of a tooth.

The "upper flat table" of a tooth is the flat portion of the tooth that contacts an opposite tooth when the top and bottom jaws come together.

Toggling of a tooth means the lateral movement of a tooth.

Terms not defined herein have a meaning as would be understood by one skilled in the art looking to standard dictionaries used in the art of dentistry.

The Ring

One aspect of this invention is a flexible, open-ended ring, with top and bottom surfaces, each forming a plane, the ring having two downward extending tines, permanently incorporated into the open ends of the ring, each tine at an obtuse angle from the bottom plane of the ring. Each tine has a top edge, a bottom edge, an outward edge, an inward edge, an inner face, and an outer face, said bottom edge of each tine converging towards the other. The fact that the bottom edge of each tine converges towards the other allows for the ring to be far more retentive than other state of the art rings.

Certain preferred aspects of the flexible, open-ended ring are shown in FIGS. 1 through 8. The embodiment illustrated in FIG. 1 shows a flexible open-ended ring 1. The shape of the ring includes, but is not limited to, circular, oval, triangular, rectangular, square or oblong. Preferably it is circular as shown. The ring is preferably an autoclavable material selected from the group consisting of alloy, chrome, stainless steel, rubber and plastic. Autoclaving allows for sterilization of the ring. Alternatively, the ring can be sterilized by treatment with alcohol or other disinfectants. The ring is flexible enough to expand to fit around a tooth being prepared for restoration and has an internal tension sufficient to hold a shield in place near the tooth as discussed hereinafter. The range or flexibility of the open-ended ring 1 is shown by two sets of arrows 2a and 2b, at the top and bottom of tines 8 and 9. The direction of flexibility of the open-ended ring 2 is shown to be generally parallel to the plane 5a formed by the top 5 surface of the ring, shown by the dotted lines and bottom plane 6a formed by the bottom surface 6 of the ring, shown by the broken lines. The diameter of the ring is such to fit into the mouth of a patient and around a tooth. Generally the size of the ring will be about 5 to 30 millimeters in diameter, preferably about 10 to 20 millimeters in diameter. The height 3 of the band of the ring 1 along with the diameter 4 of the ring 1 are shown in FIG. 1. The height 3 of the ring 1 is between about 1.0 to 5.0 millimeters. The thickness of the ring is defined as the difference between the outer face and the inner face of the band of the ring. The thickness of the ring 1 is between about 1.0 to 5.0 millimeters. The flexible open-ended ring 1 has a first downward extending tine 8 and a second downward extending tine 9. Both first 8 and second 9 downwardly extending tines have identical dimensions. Both first 8 and second 9 downwardly extending tines contain smooth edges and faces as shown in FIGS. 1 through 6 and 8. Each tine is at an obtuse angle, preferably ranging from about 95 degrees to 120 degrees from the plane of the bottom surface 6 of the ring. This is shown in side view of the ring of this invention in FIG. 9B, as compared to the 90° angle of the prior art ring shown in FIG. 9A. Downwardly extending tine 9 is incorporated into the open-ended ring 1 at 10. The length 11 of the tine 9 is measured from the bottom plane of the ring 6 to the bottom edge of the tine 14, and is between about 2.0 to 8.0 millimeters. Tine 8 will have the same dimensions. First tine 8 has a top edge 12, a bottom edge 15, an inward edge 17, an outward edge 22, an inner face 24, and an outer face 26, not visible in FIG. 1. The inner face 24 and outer face 26 of first tine 8 are shown in FIG. 4 as a top view. Second tine 9 has a top edge 28, a bottom edge 14, an inward edge 16, an outward edge 23, an inner face 25 (not visible in FIG. 1), and an outer face 27. The inner face 25 and outer face 27 of second tine 9 are shown in FIG. 5 as a top view. The top edge 28 of the second tine 9 curves downward 13 towards the bottom edge 14 of the tine. The top edge of the first tine 8 also similarly curves downward towards the bottom edge 15 of the tine. First tine 8 inward edge 17 and second tine 9 inward edge 16 are illustrated in FIGS. 1, 2 and 3. First tine 8 bottom edge 15 and second tine 9 bottom edge 14 are each essentially at a 90 degree angle to first tine 8 outward edge 22 and second tine 9 outward edge 23, respectively. One preferred embodiment illustrated in FIG. 2 shows a front view of a ring 1 with an inward edge 16 of second tine 9 converging towards the other inward edge 17 of first tine 8. A second preferred embodiment illustrated in FIG. 3 shows a front view of a ring 1 with an inward edge 16 of second tine 9 diverging away from the other inward edge 17 of first tine 8. The converging or diverging orientations of the inward edges of the tines allow the ring to be used in both the normal or inverted orientation. The normal orientation being such that the bottom edge of each tine is closest to the bottom of the tooth. The inverted orientation being that the top edge of each tine is closest to the bottom of the tooth. First tine 8 outward edge 22 is shown in FIGS. 1, 4 and 5. Second tine 9 outward edge 23 is shown in FIGS. 1, 4 and 5. First tine 8 inner face 24 is shown in FIGS. 1, 4 and 5. Second tine 9 inner face 25 is shown in FIGS. 4 and 5. The inner face of each of the tines can be made flat by techniques know in the art, e.g. extrusion, casting, blow molding, and machining. The flat-sided inner face of each tine allows for better separation of two teeth, and can be used for both normal and wide preparations. First tine 8 outer face 26 is shown in FIGS. 4 and 5. Second tine 9 outer face 27 is shown in FIGS. 1, 4 and 5. In FIG. 4, the outer edges 22 and 23 of tines 8 and 9, respectively are angled away from each other. In FIG. 5, the outer edges 22 and 23 of tines 8 and 9, respectively, are angled toward each other.

A second aspect of this invention is a method of preparing a tooth for restoration, which comprises placing a shield between two or more teeth, one tooth being a select tooth for restoration, whereas the select tooth has an upper flat table;

inserting between the select tooth and a tooth adjacent to the select tooth, a flexible, open-ended ring, with top and bottom surfaces, each forming a plane, the ring having two downward extending tines, permanently mounted to the open ends of the ring, each tine at an obtuse angle from the bottom plane surface of the ring, wherein each tine has a top edge, a bottom edge, an outward edge, an inward edge, an inner face, and an outer face, said bottom edge of each tine converging towards the other; and causing said tines of said ring to gently press the select tooth away from the adjacent tooth, and to secure the shield against the select tooth. This aids in reducing toggling of the tooth.

This aspect of the invention is illustrated in part in FIG. 6. FIG. 6 shows the use of an open-ended ring 1 and a shield 32 in the preparation of a select tooth 29 for restoration. The shield 32 is placed between the select tooth 29 and an adjacent tooth 30. The shield is also referred to as a matrix and is a thin, flexible material that can be retained in place by the ring. The shield is not more than about a millimeter thick, generally less. The bottom plane of surface 6 of the ring 1 is shown at an acute angle from the upper flat table 31 of the select tooth 29. Preferably, the bottom plane formed by surface 6 of the ring 1 is at an angle ranging from about 10 to 25 degrees from the upper flat table 31 of the select tooth 29. An optional wedge 33 is illustrated in FIG. 7, in conjunction with a shield 32 being placed between a select tooth 29 and an adjacent tooth 30. Types of wedges that can be used are Cure Thru, a clear wedge, wooden, a custom wedge, or any other wedge known in the art. The shield can include, but is not limited to, an autoclavable material selected from the group consisting of alloy, chrome, stainless steel, rubber and plastic. Autoclaving allows for sterilization of the shield. Alternatively, the shield can be sterilized by treatment with alcohol or other disinfectants. Shield shape can be elliptical, kidney-shaped, rod-like, oblong, square or rectangular. While the ring shown in FIG. 6 is singular, a plurality of shields 32 and rings 1 can be employed as illustrated in FIG. 8. FIG. 8 illustrates the usage of two open-ended rings 1 and two shields 32 in restoring a select tooth 29. The angle formed between the bottom plane surface 6 of the ring 1 and table 31 of the select tooth 29, allows for stacking of two or more rings, and clearance over obstacles like shields or wedges. A modification, as described above, of FIG. 8 would be wherein one or more rings are in an inverted position relative to the other ring or rings.

A third aspect of this invention is a kit for preparing teeth for restoration, comprising one or more flexible, open-ended rings with top and bottom surfaces, each forming a plane, each ring having two downward extending tines, permanently incorporated into the open ends of the ring, each tine at an obtuse angle from the bottom plane surface of the ring, wherein each tine has a top edge, a bottom edge, an outward edge, an inward edge, an inner face, and an outer face, said bottom edge of each tine converging towards the other; and, optionally,
   one or more shields.

The kit for preparing teeth for restoration, comprises one or more flexible, open-ended rings 1 and one or more shields 32. The open-ended ring 1 can be sold in a kit with one or more rings 1 and one or more shields 32. The open-ended ring 1 can also be sold separately or in a package of a select number. A kit may also include one or more wedges.

The ring of the invention can be made by techniques known in the art, such as extrusion, casting, blow molding, heat treating, and machining.

The shield and wedge are known in the art and can be obtained from companies such as Danville Materials, Garrison Dental Solutions, Inc., and other companies.

Instruments for inserting a ring, a wedge or a shield between two teeth, are known in the art and can be obtained from companies such as Danville Materials, Garrison Dental Solutions, Inc., and other companies. Instruments such as rubber dam clamp forceps, Howe pliers, dressing forceps, hemostat, or a cotton plier can be used to insert the ring, wedge, or shield between two teeth.

Having completed the description of the ring and its method of use, in both its broad aspects, as well as its preferred aspects, one of ordinary skill in the art may identify other aspects of the invention that would be apparent and obvious to one upon reading the specification. Such aspects of the invention are meant to be included within the scope of this disclosure and claims.

What is claimed is:

1. A flexible, open-ended ring, with top and bottom surfaces, each forming a plane, the ring having two downward extending tines, permanently incorporated into the open ends of the ring, each tine at an obtuse angle from the bottom plane surface of the ring, wherein each tine has a top edge, a bottom edge, an outward edge, an inward edge, an inner face, and an outer face, said bottom edge of each tine converging towards the other.

2. The ring of claim 1, wherein the tines are at an angle ranging from about 95 degrees to 120 degrees from the bottom plane surface of the ring.

3. The ring of claim 1, wherein the ring shape is circular.

4. The ring of claim 1, wherein the ring comprises an autoclavable material.

5. The ring of claim 1, wherein the top edge of each tine is curved downward from the top planar surface of the ring.

6. The ring of claim 1, wherein the outward edge of a tine diverges away from the outward edge of the other tine.

7. The ring of claim 1, wherein the outward edge of a tine converges towards the outward edge of the other tine.

8. The ring of claim 1, wherein the inward edge of a tine diverges away from the inward edge of the other tine.

9. The ring of claim 1, wherein the inward edge of a tine converges towards the inward edge of the other tine.

10. A method of preparing a tooth for restoration, which comprises:

(a) placing a shield between two or more teeth, one tooth being a select tooth for restoration, wherein the select tooth has an upper flat table;
   (b) inserting between the select tooth and a tooth adjacent to the select tooth, a flexible, open-ended ring, with top and bottom surfaces, each forming a plane, the ring having two downward extending tines, permanently mounted to the open ends of the ring, each tine at an obtuse angle from the bottom plane surface of the ring, wherein each tine has a top edge, a bottom edge, an outward edge, an inward edge, an inner face, and an outer face, the bottom edge of each tine converging towards the other; and
   (c) causing the tines of the ring to gently press the select tooth away from the adjacent tooth, and to secure the shield against the select tooth.

11. The method of claim 10, wherein one or more said rings are used in the method concurrently.

12. The method of claim 11, wherein one or more rings are in an inverted position relative to the other ring or rings.

13. The method of claim 10, wherein the bottom plane surface of the inserted ring is at an acute angle from the table of the select tooth.

14. The method of claim 10, wherein the bottom plane surface of the inserted ring is at an angle ranging from about 10 to 25 degrees from the table of the select tooth.

15. The method of claim 10, wherein the shield comprises an autoclavable material.

16. The method of claim 10, wherein the tines are at an angle ranging from about 95 to 120 degrees from the bottom plane surface of the ring.

17. The method of claim 10, wherein the ring shape is circular.

18. The method of claim 10, wherein the top edge of each tine is curved downward from the top planar surface of the ring.

19. The method of claim 10, wherein the outward edge of a tine diverges away from the outward edge of the other tine.

20. The method of claim 10, wherein the outward edge of a tine converges towards the outward edge of the other tine.

21. The method of claim 10, wherein the inward edge of a tine diverges away from the inward edge of the other tine.

22. The method of claim 10, wherein the inward edge of a tine converges towards the inward edge of the other tine.

23. A kit for preparing teeth for restoration, comprising:

(a) one or more flexible, open-ended rings with top and bottom surfaces, each forming a plane, each ring having two downward extending tines, permanently incorporated into the open ends of the ring, each tine at an obtuse angle from the bottom plane surface of the ring, wherein each tine has a top edge, a bottom edge, an outward edge, an inward edge, an inner face, and an outer face, the bottom edge of each tine converging towards the other; and (b) one or more shields designed for use with the open-ended rings.

* * * * *